(12) United States Patent
Shabaan et al.

(10) Patent No.: US 11,724,991 B1
(45) Date of Patent: Aug. 15, 2023

(54) SELECTIVE 5-LO INHIBITORS FOR THE TREATMENT OF BRONCHIAL ASTHMA

(71) Applicant: KING FAISAL UNIVERSITY, Al-Ahsa (SA)

(72) Inventors: Saadeldin Elsayed Ibrahim Shabaan, Al-Ahsa (SA); Hany Mohamed Abd El-Lateef Ahmed, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/094,113

(22) Filed: Jan. 6, 2023

(51) Int. Cl.
 *C07D 257/04* (2006.01)
 *C07D 403/10* (2006.01)

(52) U.S. Cl.
 CPC ......... *C07D 257/04* (2013.01); *C07D 403/10* (2013.01)

(58) Field of Classification Search
 None
 See application file for complete search history.

(56) References Cited

U.S. PATENT DOCUMENTS

2006/0106014 A1  5/2006  Boddupalli et al.
2010/0081684 A1  4/2010  Boyce et al.

OTHER PUBLICATIONS

Boschi et al., "Multitarget Drugs: Synthesis and Preliminary Pharmacological Characterization of Zileuton Analogues Endowed with Dual 5-LO Inhibitor and NO-Dependent Activities," Chem Med Chem, (5)9: pp. 1444-1449 (2010).
2-Methylbenzoylacetonitrile, PubChem, 2005.
Werz, O., & Steinhilber, D., "Pharmacological intervention with 5-lipoxygenase: new insights and novel compounds," Expert Opin. Ther. Patents 15(5): pp. 505-519 (2005).
Maucher, I., et al., "Michael acceptor containing drugs are a novel class of 5-lipoxygenase inhibitor targeting the surface cysteines C416 and C418," Biochemical Pharmacology, 125(1): pp. 55-74 (2004).
Connoll, P., et al., "N-Hydroxyurea and Hydorxamic Acid Inhibitors of Cyclooxygenase and 5-Lipoxygenase," Bioorganic & Medicinal Chemistry Letters, 9: pp. 979-984 (1999).

*Primary Examiner* — Craig D Ricci

(74) *Attorney, Agent, or Firm* — Nath, Goldberg & Meyer; Richard C. Litman

(57) ABSTRACT

Novel dual 5-LO inhibitors of well validated electrophilic Michael acceptors and nitrogen-heterocycles are presented and designed to maintain specific structural features of currently known dual 5-LO inhibitors and to overcome their drawbacks. The Michael acceptor scaffold will act as a carrier and will provide a stable anchorage via covalent binding to cysteine/histidine residues within the catalytic cleft and/or the surface interface of the 5-LO; whereas, the nitrogen-heterocycles will ensure the access to the Fe(II) catalytic center. These combinations offer potential for more than one mode of iron chelation and 5-LO inhibition.

16 Claims, No Drawings

SELECTIVE 5-LO INHIBITORS FOR THE TREATMENT OF BRONCHIAL ASTHMA

BACKGROUND

1. Field

The disclosure of the present patent application relates to novel dual 5-LO (5-lipoxygenase) inhibitors of well validated electrophilic Michael acceptors and nitrogen-heterocycles that are useful in treating various acute and/or chronic airway diseases or disorders.

2. Description of the Related Art

Lipoxygenases are nonheme iron-containing enzymes found in plants and animals that catalyze the oxygenation of certain polyunsaturated fatty acids, such as lipids and lipoproteins. Several different lipoxygenase enzymes are known, each having a characteristic oxidation action. Mammalian lipoxygenases are named by the position in arachidonic acid that is oxygenated. The enzyme 5-lipoxygenase converts arachidonic acid to 5-hydroperoxy-eicosatetraenoic acid (5-HPETE). This is the first step in the metabolic pathway which yields 5-hydroxyeicosatetraenoic acid (5-HETE) and the leukotrienes (LTs). Similarly, 12- and 15-lipoxygenase convert arachidonic acid to 12- and 15-HPETE, respectively. Biochemical reduction of 12-HPETE leads to 12-HETE, while 15-HETE is the precursor of the class of compounds known as lipoxins.

A diverse array of biological effects is associated with the products of lipoxygenase activity, and many are implicated as mediators in various disease states. The C4 and D4 leukotrienes are potent constrictors of human bronchial smooth muscle; LTB4 and 5-HETE, found in the synovial fluid of patients with rheumatoid arthritis, are potent chemotactic factors for inflammatory cells such as polymorphonuclear leukocytes (Green and Lambeth. Tetrahedron, Vol. 39 (1983), pp. 1687); 12-HETE has been found at high levels in the epidermal tissue of patients with psoriasis; and the lipoxins have been shown to stimulate liposomal enzyme and superoxide ion release from neutrophils. Thus, lipoxygenase enzymes play an important role in the biosynthesis of mediators of asthma, allergy, arthritis, psoriasis, and inflammation, and inhibitors of these enzymes interrupt the biochemical pathway involved in these disease states.

Human 15-lipoxygenase (15-LO) catalyzes the formation of 15-S-hydroxyeicosatetraenoic acid (15-S-HETE) from arachidonic acid (Kuhn and Borngraber. Lipoxygenases and Their Metabolites. New York, Plenum Press, 1999). In mice, the synthesis of 15-S-HETE is carried out by 12/15-Lipoxygenase which is the murine homologue of human 15-LO. Murine 12/15-LO converts arachidonic acid to 12(S)-hydroxyeicosatetraenoic and 15-S-HETE in a 3:1 ratio and can additionally convert linoleic acid to 13-hydroxyoctadecadienoic acid (13-HODE).

15-Lipoxygenase has previously been implicated in the pathogenesis of several diseases, including atherosclerosis (Harats et al. Arterioscler. Thromb. Vasc. Biol., 2000, pp. 2100-2105), asthma (Shannon et al. Am. Rev. Respir. Dis., Vol. 147 (1993), pp. 1024-1028), cancer (Shureiqi et al. JNCI, Vol. 92 (2000), pp. 1136-1142), and glomerulonephritis (Montero and Bard. Exp. Neph., Vol. 8 (2000), pp. 14-19). A number of classes of compounds have been identified that inhibit 15-LO, including phenols, hydroxamic acids and acetylenic fatty acids (reviewed in Kuhn and Borngraber. Lipoxygenases and Their Metabolites. New York, Plenum Press, 1999). The spectrum of inhibitory activities varies for these agents. For example, nordihydroguaiaretic acid (NDGA) has been shown to be an inhibitor of 5- and 15-lipoxygenase, naphthyl hydroxamic acids have been shown to inhibit 5-, 12-, and 15-lipoxygenase (U.S. Pat. No. 4,605,669), a benzofluorene 15-LO inhibitor, PD146176, has been reported to be relatively specific for the 15-LO enzyme (Sendobry et al. Br. J. Pharm., Vol. 120 (1997), pp. 1199-1206), and a benzothiophene 5-LO inhibitor, A-64077, (Zileuton, U.S. Pat. No. 4,873,259) has been reported to be specific for the 5-LO enzyme (see e.g., Bell R. L. et al. Int. J. Immunopharmacol., Vol. 14, no. 3 (1992), pp. 505-10).

Bronchial asthma is a serious health problem all over the world. 5-10% of people of all ages have a chronic airway disorder. Likewise, respiratory distress syndrome is the main common manifestations of coronavirus 2 (SARS-CoV-2) infection. Although vaccination can prevent people from getting seriously ill or dying, there is no vaccine which conveys 100% protection. Further, there remains a lack of strategies being conducted to overcome asthma exacerbation caused by SARS-CoV-2 infection. As noted, over the last decade, it has become clear that 5-lipoxygenase (5-LO) inhibitors play key roles in inflammatory responses and have been widely explored as possible treatment for asthma and respiratory viral infections. 5-LO inhibitors might therefore be beneficial to reduce COVID-19 patient mortality rate and may help prevent disease progression and severity.

Zileuton is the only 5-LO inhibitor drug that has currently reached the market, but with limited clinical use due to its weak inhibitory efficacy (e.g., $IC_{50}$=0.5-1 μM in stimulated leukocytes), poor bioavailability/pharmacokinetics (e.g., short serum half-life of 3 hrs and strong plasma protein binding of 93%), and undesirable side effects (e.g., hepatoxicity). Therefore, there is an urgent need to develop more efficient and selective 5-LO inhibitors with improved pharmacokinetic properties, particularly for the treatment of bronchial asthma.

Thus, new 5-LO inhibitors solving the aforementioned problems are desired.

SUMMARY

The present subject matter is directed to novel 5-LO inhibitors which can be used for treating various acute or chronic airway diseases or disorders.

In one embodiment, the present subject matter relates to a compound having the formula I:

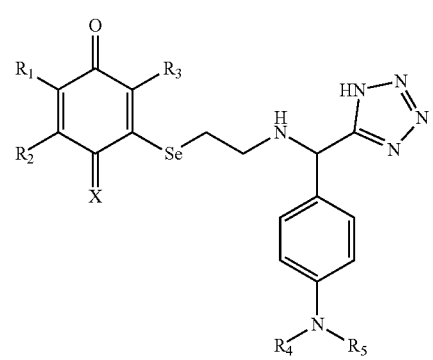

or a pharmaceutically acceptable salt, ester, stereoisomer, or solvate thereof, wherein X is O or $NR_6$, wherein $R_6$ is acetyl;

$R_1$ and $R_2$ are independently hydrogen, straight or branched $C_1$-$C_6$ alkyl, or straight or branched $C_2$-$C_6$ alkenyl, or wherein $R_1$ and $R_2$ can be taken together, along with the carbon atoms to which they are attached, to form a phenyl ring;

$R_3$ is hydrogen, straight or branched $C_1$-$C_6$ alkyl, or straight or branched $C_2$-$C_6$ alkenyl; and $R_4$ and $R_5$ are independently hydrogen, straight or branched $C_1$-$C_6$ alkyl, straight or branched $C_2$-$C_6$ alkenyl, or are taken together to form a $C_1$ alkenyl, wherein said straight or branched $C_1$-$C_6$ alkyl, straight or branched $C_2$-$C_6$ alkenyl, or $C_1$ alkenyl is unsubstituted or can be substituted with one or more substituents independently selected from the group consisting of an unsubstituted phenyl ring, a substituted phenyl ring, an unsubstituted tetrazole ring, or a substituted tetrazole ring, or wherein $R_4$ and $R_5$ can be taken together, along with the nitrogen atom to which they are attached, to form a maleimide group.

In another embodiment, the present subject matter relates to a compound having the formula I:

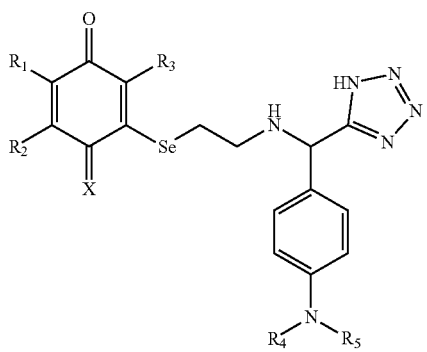

I or a pharmaceutically acceptable salt, ester, stereoisomer, or solvate thereof, wherein X is O or $NR_6$, wherein $R_6$ is acetyl;

$R_1$ is hydrogen, $R_2$ is hydrogen or isopropyl, or wherein $R_1$ and $R_2$ can be taken together, along with the carbon atoms to which they are attached, to form a phenyl ring;

$R_3$ is hydrogen or methyl; and $R_4$ is hydrogen, $R_5$ is hydrogen or methyl substituted with a phenyl ring and a tert-butyl substituted tetrazole ring, $R_4$ and $R_5$ are taken together to form a $C_1$ alkenyl substituted with a phenyl ring, or $R_4$ and $R_5$ are taken together, along with the nitrogen atom to which they are attached, to form a maleimide group.

In a further embodiment, the present subject matter relates to a compound selected from the group consisting of:

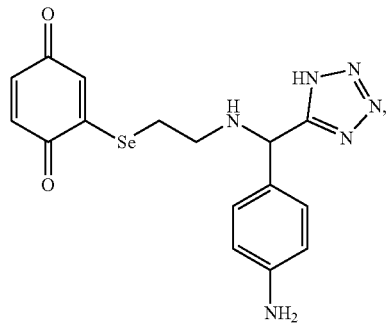

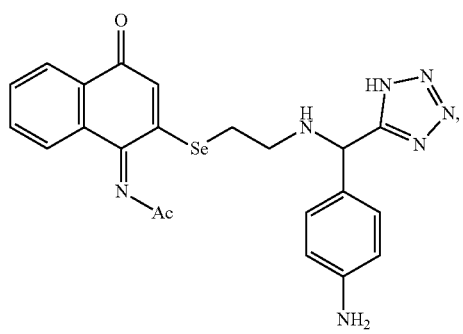

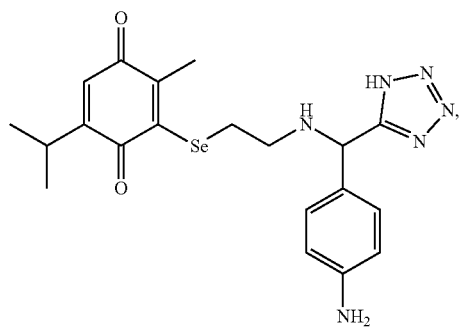

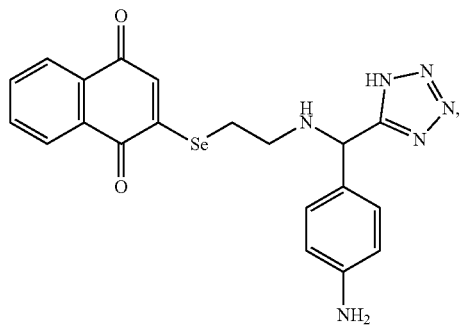

5
-continued
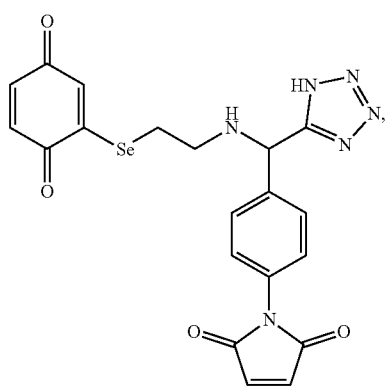
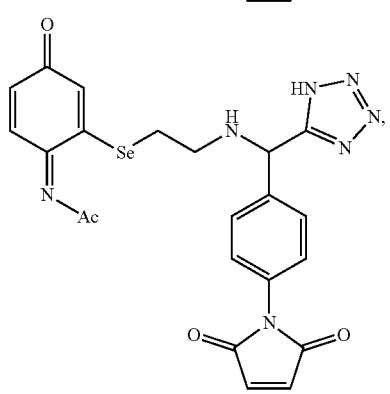
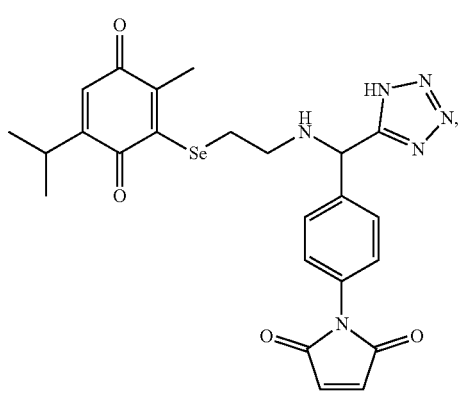
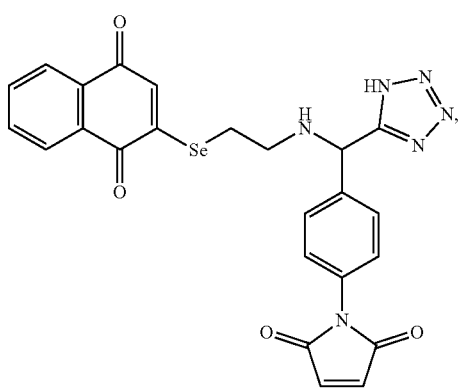
6
-continued
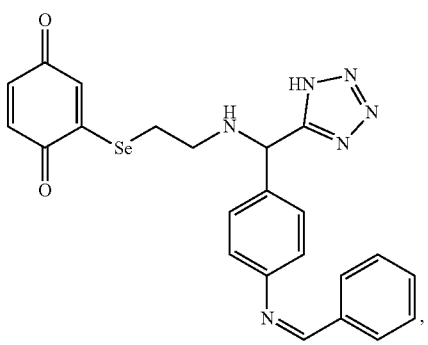
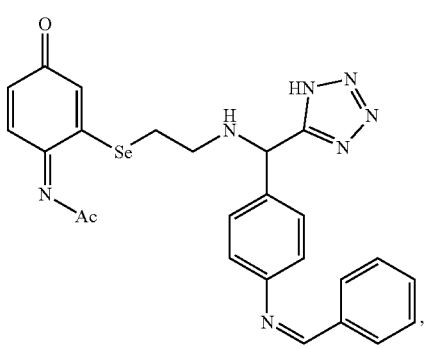
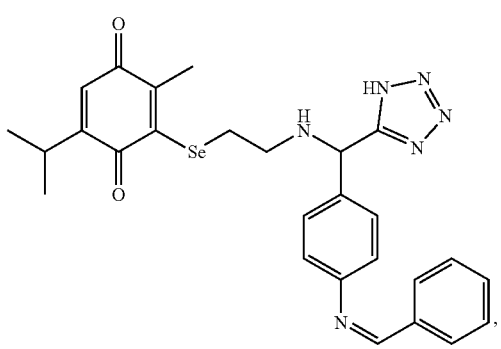
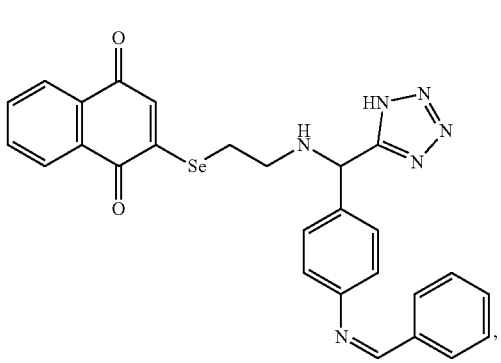

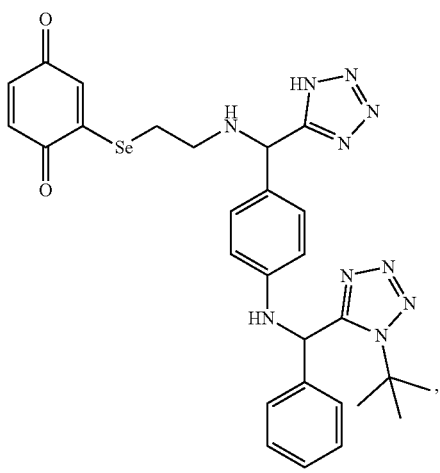

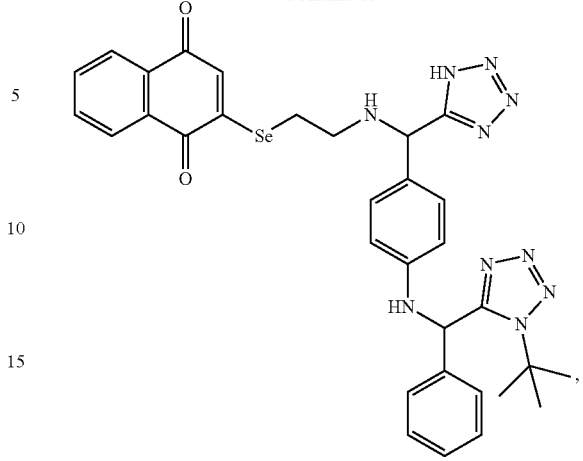

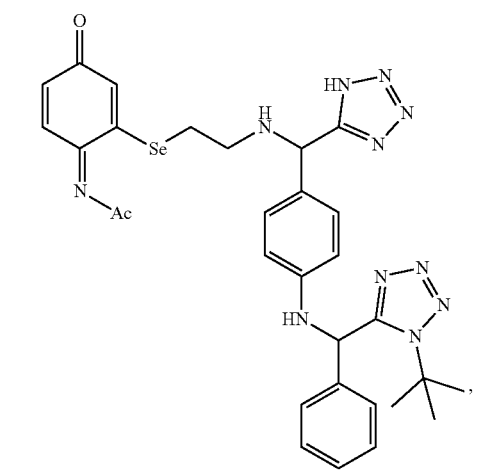

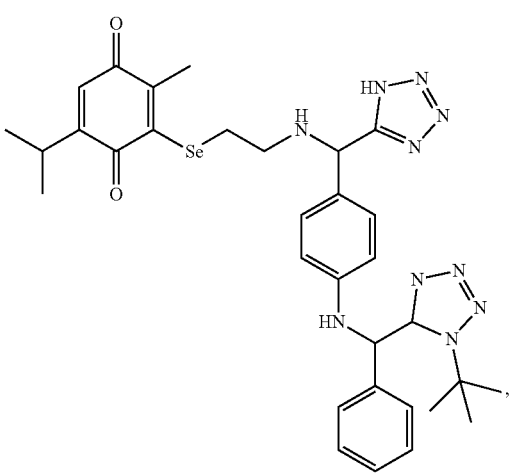

and a pharmaceutically acceptable salt, ester, stereoisomer, or solvate thereof.

Further contemplated herein are pharmaceutical compositions containing these compounds, as well as methods of treating various acute or chronic airway diseases or disorders by administering the present compounds to a patient in need thereof.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., C1-40 alkyl group), for example, 1-30 carbon atoms (i.e., C1-30 alkyl group). In some embodiments, an alkyl group can have 1 to 6 carbon atoms, and can be referred to as a "lower alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-40 alkenyl group), for example, 2 to 20 carbon atoms (i.e., C2-20 alkenyl group). In some embodiments, alkenyl groups can be substituted as described herein. An alkenyl group is generally not substituted with another alkenyl group, an alkyl group, or an alkynyl group.

The term "substituted alkyl" as used herein refers to an alkyl group in which 1 or more (up to about 5, for example about 3) hydrogen atoms is replaced by a substituent independently selected from the group: —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino.

The term "substituted alkenyl" refers to an alkenyl group in which 1 or more (up to about 5, for example about 3) hydrogen atoms is replaced by a substituent independently selected from those listed above with respect to a substituted alkyl.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group as a whole can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "acyl" refers to the group —C(O)—R$_7$, where R$_7$ may be selected from hydrogen, alkyl, substituted alkyl, alkenyl, substituted alkenyl, alkynyl, substituted alkynyl, cycloalkyl, substituted cycloalkyl, aryl, substituted aryl, heterocyclic, and substituted heterocyclic. In this regard, an "acetyl" is an acyl group where R$_7$ is hydrogen.

The term "acyloxy" refers to the group —O-acyl, where acyl is defined herein.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as an acute or chronic airway disorder or disease.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Compounds

In one embodiment, the present subject matter relates to a compound having the formula I:

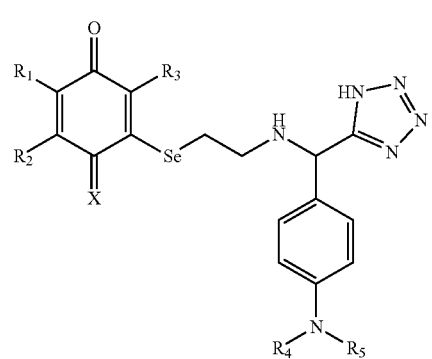

or a pharmaceutically acceptable salt, ester, stereoisomer, or solvate thereof, wherein X is O or NR$_6$, wherein R$_6$ is acetyl;

R$_1$ and R$_2$ are independently hydrogen, straight or branched C$_1$-C$_6$ alkyl, or straight or branched C$_2$-C$_6$ alkenyl, or wherein R$_1$ and R$_2$ can be taken together, along with the carbon atoms to which they are attached, to form a phenyl ring;

R$_3$ is hydrogen, straight or branched C$_1$-C$_6$ alkyl, or straight or branched C$_2$-C$_6$ alkenyl; and R$_4$ and R$_5$ are independently hydrogen, straight or branched C$_1$-C$_6$ alkyl, straight or branched C$_2$-C$_6$ alkenyl, or are taken together to form a C$_1$ alkenyl, wherein said straight or branched $C_1$-$C_6$ alkyl, straight or branched $C_2$-$C_6$ alkenyl, or $C_1$ alkenyl is unsubstituted or can be substituted with one or more substituents independently selected from the group consisting of an unsubstituted phenyl ring, a substituted phenyl ring, an unsubstituted tetrazole ring, or a substituted tetrazole ring, or wherein $R_4$ and $R_5$ can be taken together, along with the nitrogen atom to which they are attached, to form a maleimide group.

In one embodiment, the present subject matter relates to a compound of formula I, wherein $R_2$ is hydrogen, propyl, or isopropyl.

In another embodiment, the present subject matter relates to a compound of formula I, wherein $R_3$ is hydrogen or methyl.

In a further embodiment, the present subject matter relates to a compound of formula I, wherein $R_1$ is hydrogen.

In yet another embodiment, the present subject matter relates to a compound of formula I, wherein $R_1$ and $R_2$ are taken together, along with the carbon atoms to which they are attached, to form a phenyl ring.

In certain embodiments, the present subject matter relates to a compound of formula I, wherein $R_4$ is hydrogen.

In additional embodiments, the present subject matter relates to a compound of formula I, wherein $R_5$ is hydrogen or a $C_1$ alkyl or alkenyl substituted with one or more substituents.

In still another embodiment, the present subject matter relates to a compound of formula I, wherein the one or more substituents for $R_5$ are selected from the group consisting of phenyl, tetrazole, tetrazole substituted with a $C_1$-$C_6$ straight or branched chain alkyl group, and combinations thereof.

In one more embodiment, the present subject matter relates to a compound of formula I, wherein $R_5$ is a methyl substituted with a phenyl and an alkyl-substituted tetrazole.

In still yet another embodiment, the present subject matter relates to a compound of formula I, wherein $R_4$ and $R_5$ are taken together, along with the nitrogen atom to which they are attached, to form a maleimide group.

In another embodiment, the present subject matter relates to a compound of formula I, wherein the compound is selected from the group consisting of:

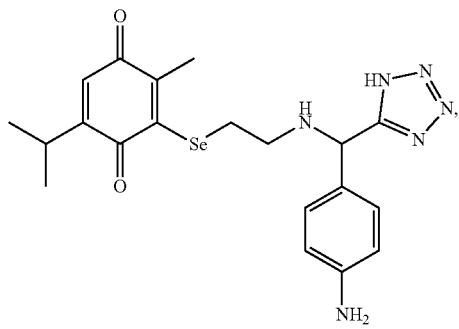

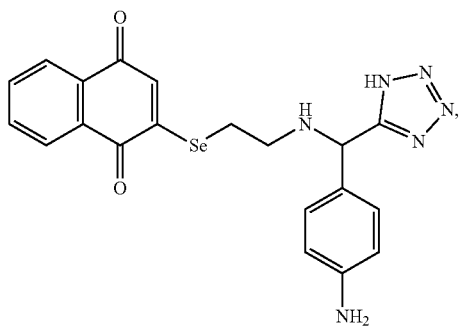

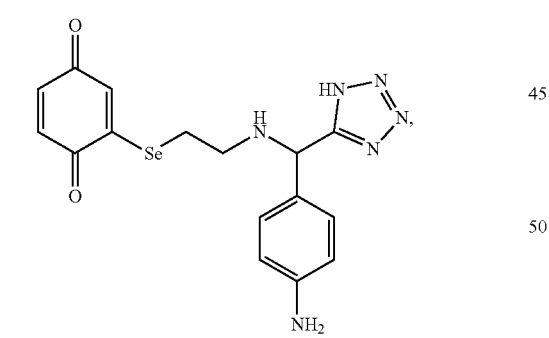

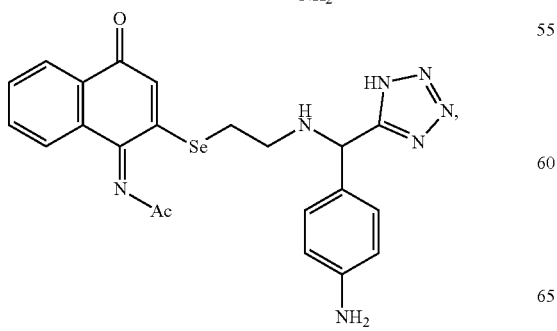

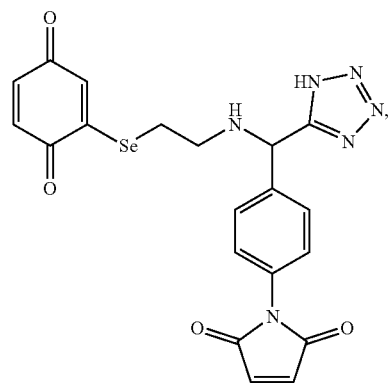

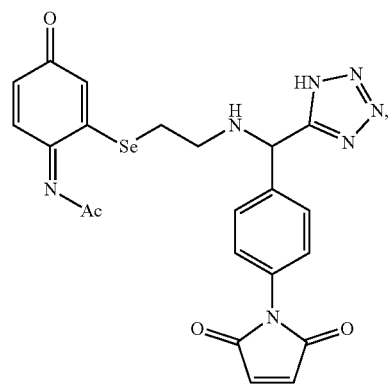

-continued
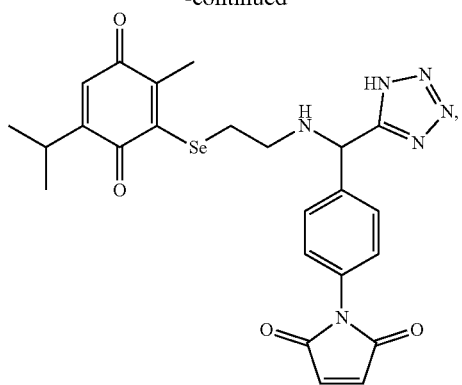
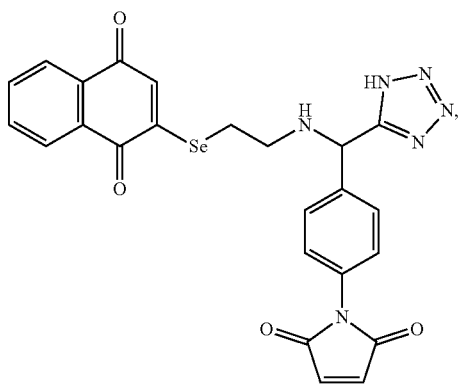
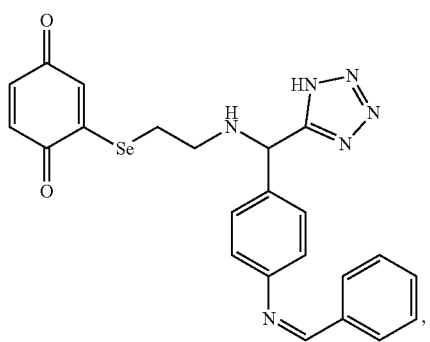
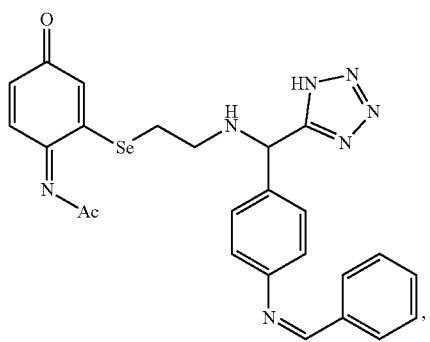
-continued
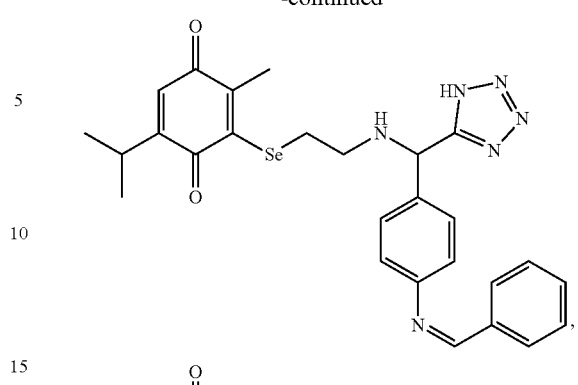
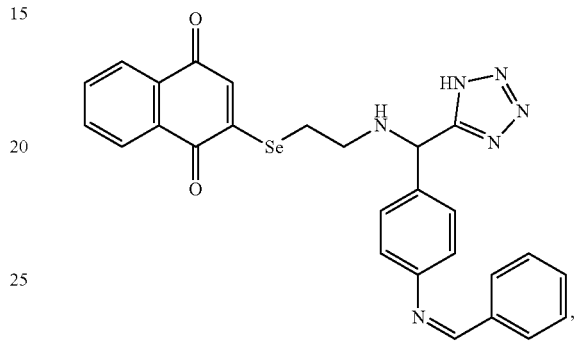
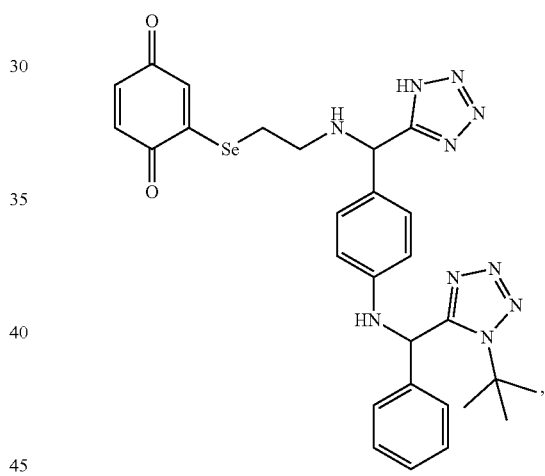
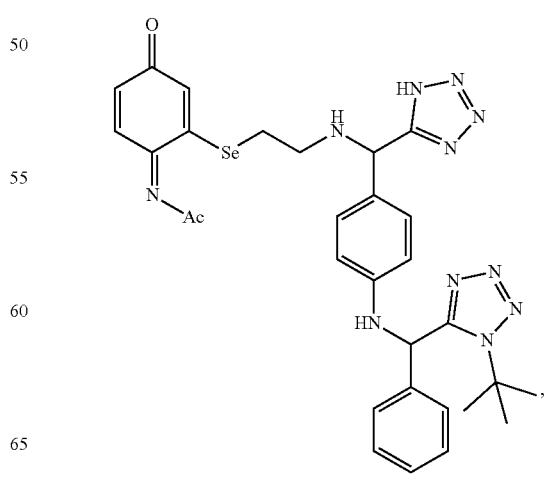

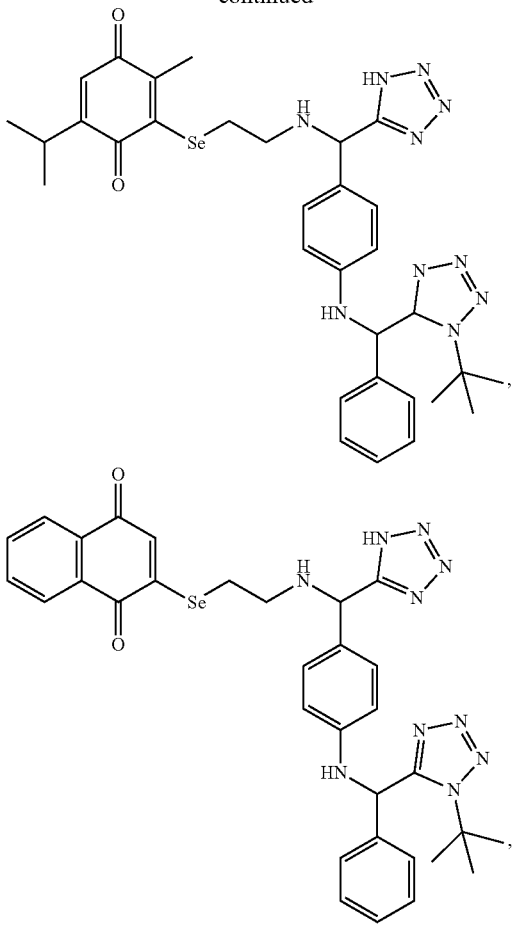

and a pharmaceutically acceptable salt, ester, stereoisomer, or solvate thereof.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or the salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phos-phates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g. when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g. by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

The sophisticated nature of inflammation related diseases, such as various acute or chronic airways diseases or disorders, calls for a proper combination of two or more "well validated" pharmacophore(s) in a single molecule in order to achieve greater effectiveness, i.e., one compound able to hit different targets simultaneously. The present subject matter relates to combining the structural features of well validated electrophilic Michael acceptors, as carriers, with suitable N-hydroxyurea/hydroxamic acid surrogates to specifically enter the catalytic cleft of 5-LO and form stable anchorage of the new ligand within the catalytic center.

The non-toxic N-hydroxyurea/hydroxamic acid scaffold ensures the access to the catalytic center whereas the Michael acceptor moiety should provide the stable anchorage via covalent modification of reactive cysteines/histidines within the catalytic cleft and/or the surface interface of the enzyme.

This innovative avenue for, e.g., bronchial asthma treatment. would overcome the frequently observed loss of affinity of many developed 5-LO inhibitors to the enzyme in inflamed tissues under in vivo conditions.

TABLE 2

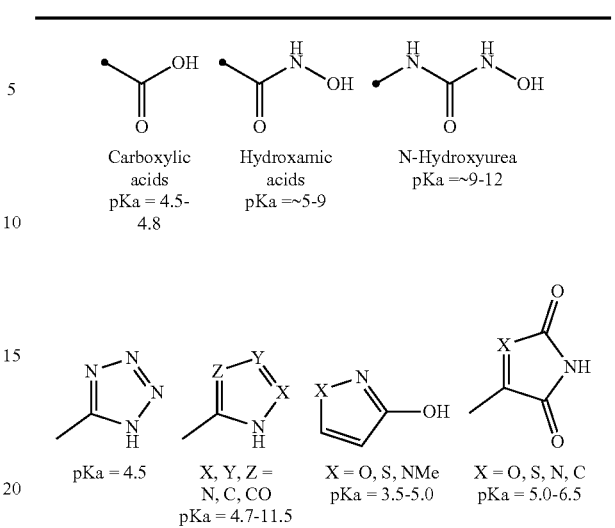

TABLE 1

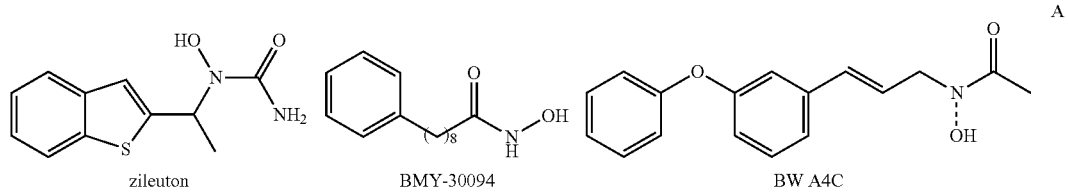

Given that different N-hydroxyureas (e.g., zileuton) and hydroxamic acid (e.g., BWA4C and BMY-30094) as identified above in Table 1 are potent 5-LO inhibitor candidates via chelation with the non-heme Fe(II) in the active site, the objective is to replace zileuton with N-hydroxyurea and hydroxamic acid isosteres, likely nitrogen-heterocycles (N-heterocycles) which are known for their improved pharmacokinetic properties, including with respect to crossing the blood-brain barrier, as per Table 2, below. The N-hydroxyurea/hydroxamic acid surrogates offer safer, simpler, and stable functionalities and at the same time should maintain the potent inhibition demonstrated by the zileuton original analogue.

In one embodiment, the present 5-LO inhibitor compounds can be prepared according to an Azido-Ugi reaction. In this regard, the below synthetic pathways provide one specific example of making the present compounds:

Scheme 1 shows the reaction of 3-bromopropylamine hydrobromide (1) with $Na_2Se_2$ (in situ prepared from elemental selenium, $NaBH_4$, and NaOH) affords the corresponding 2,2'-diselanediylbis(ethan-1-amine) (2) (Scheme 1). The latter undergoes reduction and subsequent nucleophilic substitution reaction with 2-bromonaphthalene-1,4-dione (3) to give 2-((2-aminoethyl)selanyl)naphthalene-1,4-dione (4).

Scheme 1

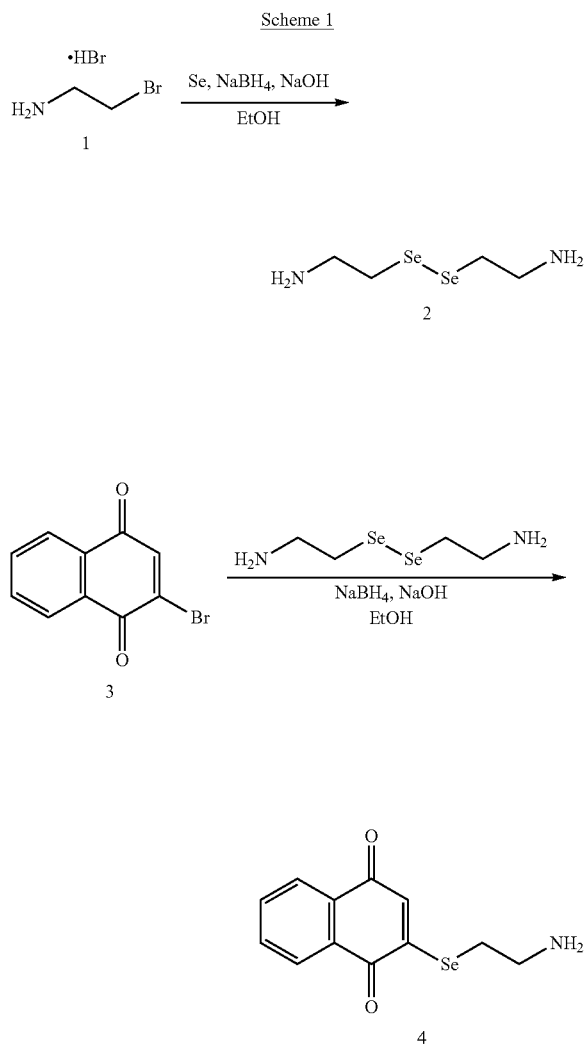

Scheme 2

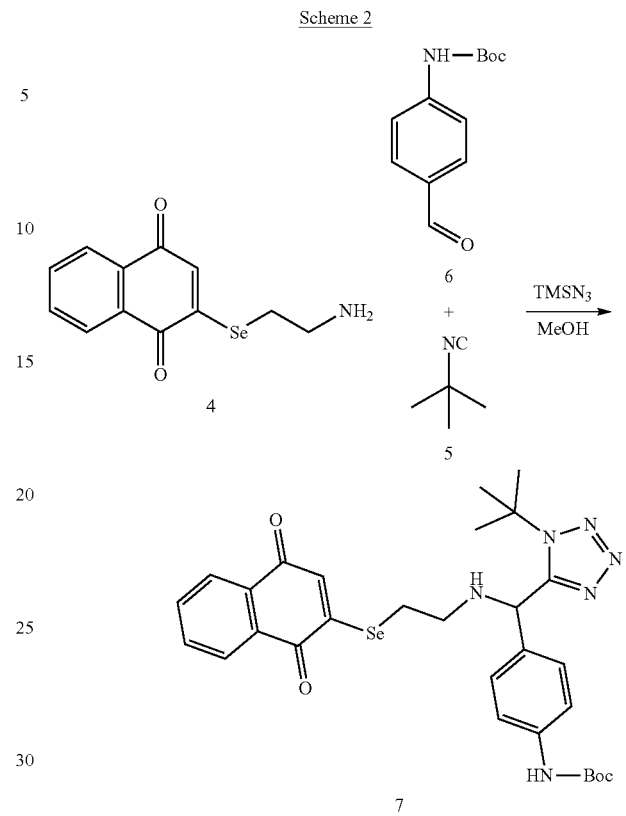

Scheme 2 shows the azido-Ugi four-components reaction of the selenium-based quinone 4 (as an amine) with tert-butyl isocyanide (5), trimethylsilyl azide, and tert-butyl (4-formyl phenyl) carbamate (6) afford the corresponding selenoquinones-based tetrazole (7).

There is plenty for derivatization; using different isocyanides and aldehydes gives access to different selenoquinones-based tetrazoles. On the other hand, as shown in Scheme 3, tetrazole 7 is a boc-protected amine which, upon cleavage under mild conditions (trifluoroacetic acid (TFA) affords the respective aromatic amine 8. The reaction of amine 8 with maleic anhydride in toluene followed by gentle heating (55° C.-60° C.) with acetic anhydride (Ac$_2$O) affords the corresponding N-maleimide 9. Furthermore, the reaction of amine 8 with different aromatic aldehydes (here, benzaldehyde is used) gives access to the Schiff base 10. Moreover, another successive four-component azido-Ugi reaction of 8, as the amine component, with tert-butyl isocyanide, trimethylsilyl azide, and benzaldehyde affords the corresponding bi-tetrazole (11).

Scheme 3

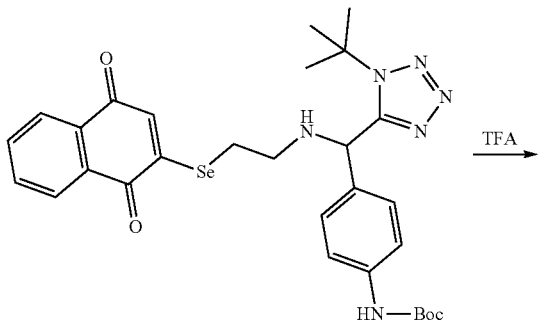

-continued

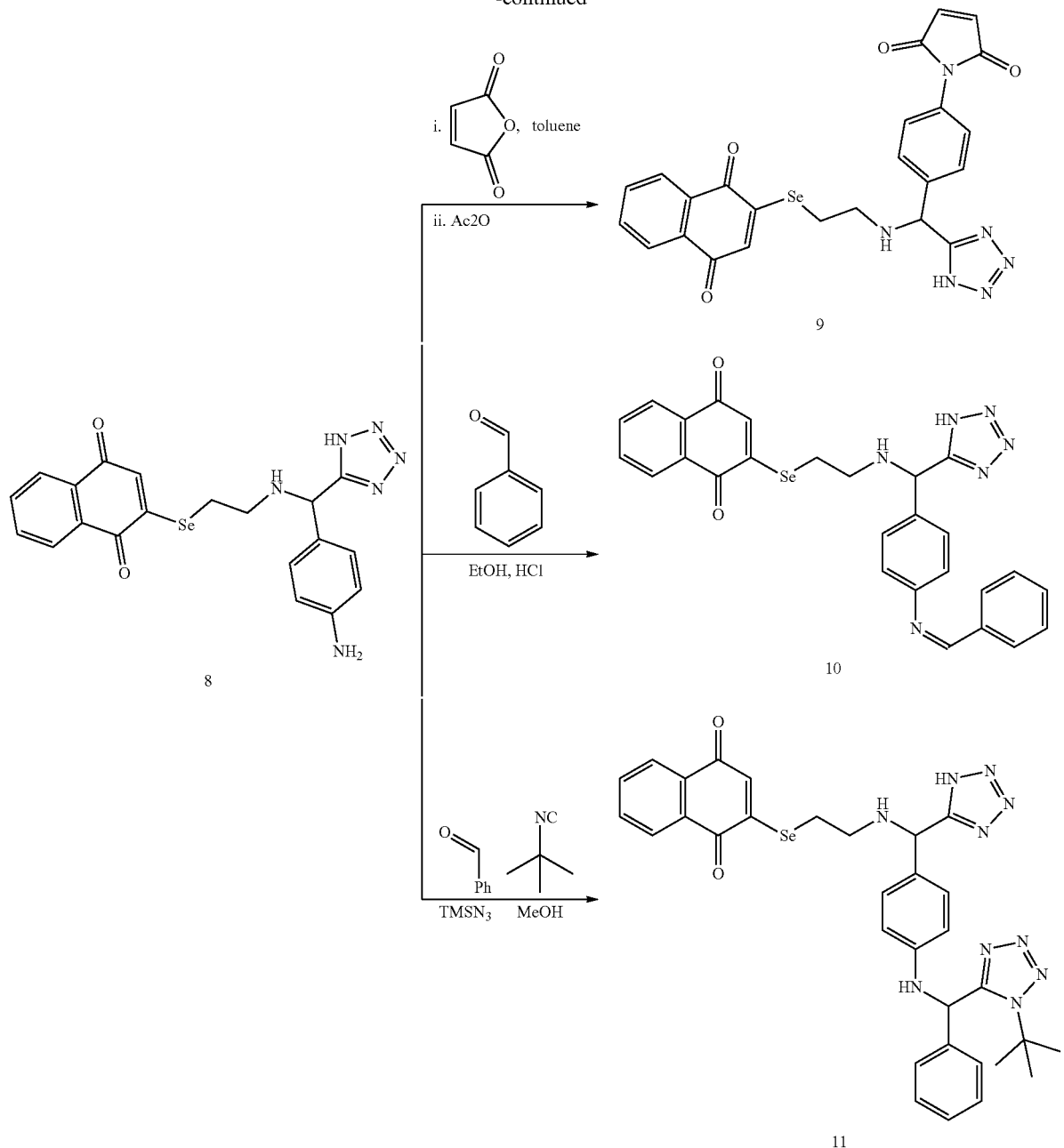

Pharmaceutical Compositions

In another embodiment, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one or two of the present compounds, or one of the present compounds.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for an acute or chronic airway disease or disorder. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of an acute or chronic airway disease or disorder, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for foods or animals, including medical foods, functional food, special nutrition foods and dietary supplements. A "medical food" is a product prescribed by a physician that is intended for the specific dietary management of a disorder or health condition for which distinctive nutritional requirements exist, and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into food stuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

Methods of Use

The present compounds have valuable pharmaceutical properties, which make them commercially utilizable. In particular, as 5-LO inhibitors, they are suitable on the one hand as bronchial therapeutics, but on the other hand especially for the treatment of disorders, in particular of an inflammatory nature, e.g., of the airways. In this context, the compounds of the invention are distinguished by valuable and desirable properties, such as, for example, high efficacy, high selectivity, low toxicity, superior bioavailability in general (e.g., good enteral absorption), superior therapeutic window, superior pharmacokinetics (e.g., half-life), absence of significant side effects, and further beneficial effects related to their therapeutic and pharmaceutical suitability.

Accordingly, the present subject matter further relates to use of the present compounds for the treatment of diseases, especially diseases alleviated by inhibition of 5-lipoxygenase (5-LO).

In this regard, the present subject matter relates to a method of treating an acute or chronic airway disease or disorder in a patient, comprising administering to a patient in need thereof a therapeutically effective amount of a compound as described herein.

In a further embodiment, the acute or chronic airway disease or disorder treatable herein can be selected from the group consisting of bronchitis, allergic bronchitis, asthma, bronchial asthma, emphysema, COPD, pulmonary hypertension, lung fibrosis, respiratory distress syndrome, respiratory viral infections, allergic rhinitis, COVID-19 respiratory symptoms, and combinations thereof.

The present subject matter also relates to the use of a compound as described herein in the manufacture of a pharmaceutical composition inhibiting 5-LO, in particular a pharmaceutical composition for the treatment of diseases or disorders alleviated by inhibition of 5-LO, such as the diseases or disorders exemplified above. In particular, the present subject matter relates to the use of a compound as described herein in the manufacture of a pharmaceutical composition for the treatment or prophylaxis of an acute or chronic airway disease, such as, but not limited to, bronchitis, allergic bronchitis, bronchial asthma, emphysema, COPD, pulmonary hypertension, lung fibrosis, or COVID-19 respiratory symptoms.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

Especially, the present subject matter relates to a method of treating or preventing a disease, which is alleviated by inhibition of 5-lipoxygenase comprising administering to a patient in need thereof a therapeutically effective amount of at least one of the compounds herein.

In an embodiment, the present subject matter relates to a method of treating an acute or chronic airway disease, for example, but not limited to, bronchitis, allergic bronchitis, bronchial asthma, emphysema, COPD, pulmonary hypertension, lung fibrosis, or COVID-19 respiratory symptoms comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one or two of the present compounds are used, or one of the present compounds is used.

It is to be understood that the 5-LO inhibitors are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A compound having the formula I:

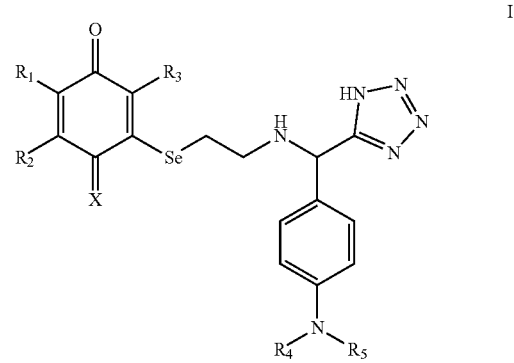

or a pharmaceutically acceptable salt, ester, stereoisomer, or solvate thereof, wherein X is O or $NR_6$, wherein $R_6$ is acetyl;

$R_1$ and $R_2$ are independently hydrogen, straight or branched $C_1$-$C_6$ alkyl, or straight or branched $C_2$-$C_6$ alkenyl, or wherein $R_1$ and $R_2$ can be taken together, along with the carbon atoms to which they are attached, to form a phenyl ring;

$R_3$ is hydrogen, straight or branched $C_1$-$C_6$ alkyl, or straight or branched $C_2$-$C_6$ alkenyl; and $R_4$ and $R_5$ are independently hydrogen, straight or branched $C_1$-$C_6$ alkyl, straight or branched $C_2$-$C_6$ alkenyl, or are taken together to form a $C_1$ alkenyl, wherein said straight or branched $C_1$-$C_6$ alkyl, straight or branched $C_2$-$C_6$ alkenyl, or $C_1$ alkenyl is unsubstituted or can be substituted with one or more substituents independently selected from the group consisting of an unsubstituted phenyl ring, a substituted phenyl ring, an unsubstituted tetrazole ring, or a substituted tetrazole ring, or wherein $R_4$ and $R_5$ can be taken together, along with the nitrogen atom to which they are attached, to form a maleimide group.

2. The compound of claim 1, wherein $R_2$ is hydrogen, propyl, or isopropyl.

3. The compound of claim 1, wherein $R_3$ is hydrogen or methyl.

4. The compound of claim 1, wherein $R_1$ is hydrogen.

5. The compound of claim 1, wherein $R_1$ and $R_2$ are taken together, along with the carbon atoms to which they are attached, to form a phenyl ring.

6. The compound of claim 1, wherein $R_4$ is hydrogen.

7. The compound of claim 1, wherein $R_5$ is hydrogen or a $C_1$ alkyl or alkenyl substituted with one or more substituents.

8. The compound of claim 7, wherein the one or more substituents for $R_5$ are selected from the group consisting of phenyl, tetrazole, tetrazole substituted with a $C_1$-$C_6$ straight or branched chain alkyl group, and combinations thereof.

9. The compound of claim 8, wherein $R_5$ is a methyl substituted with a phenyl and an alkyl-substituted tetrazole.

10. The compound of claim 1, wherein $R_4$ and $R_5$ are taken together, along with the nitrogen atom to which they are attached, to form a maleimide group.

11. The compound of claim 1, wherein the compound is selected from the group consisting of:

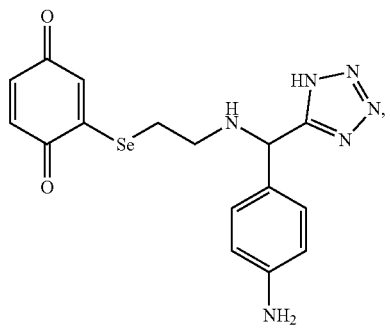

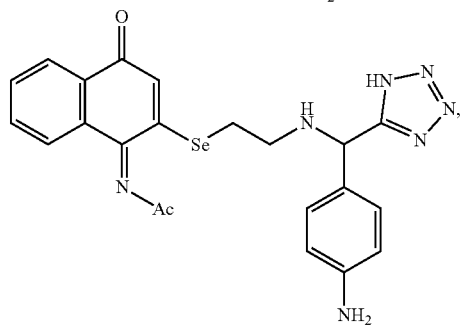

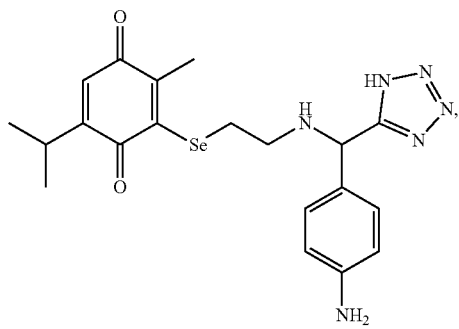

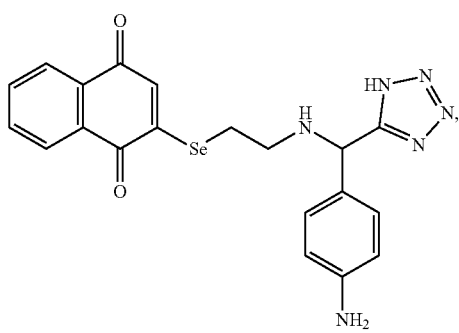

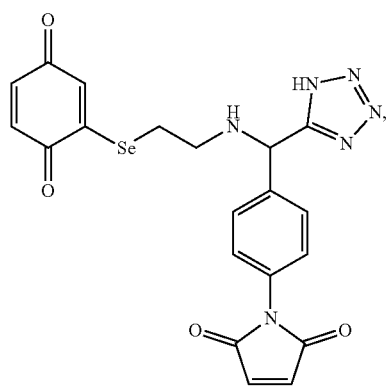

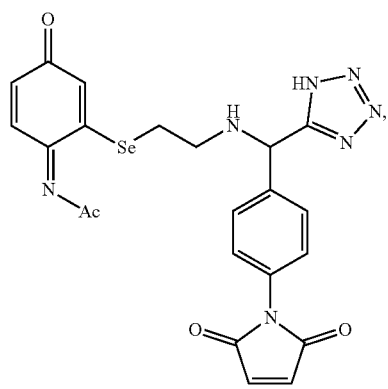

31
-continued
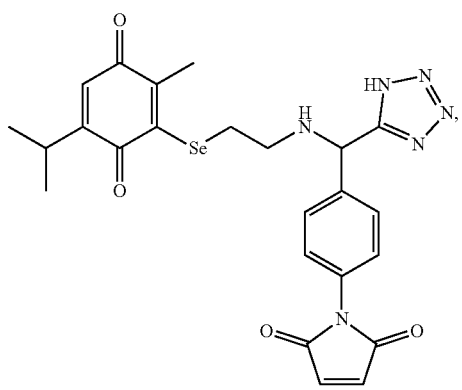
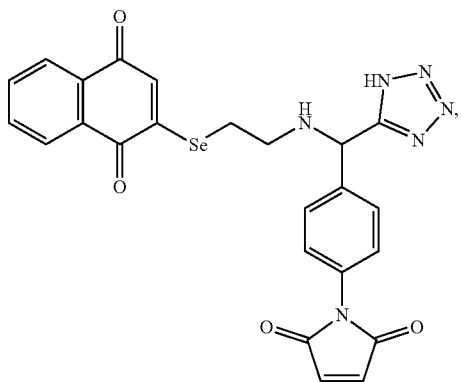
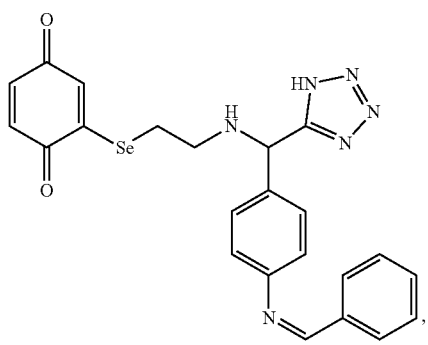
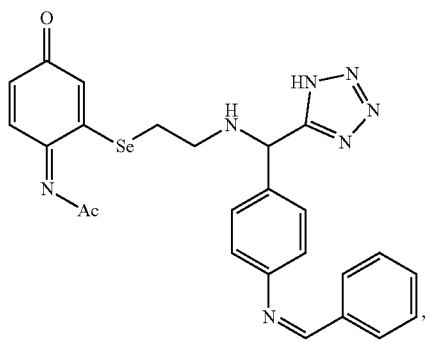
32
-continued
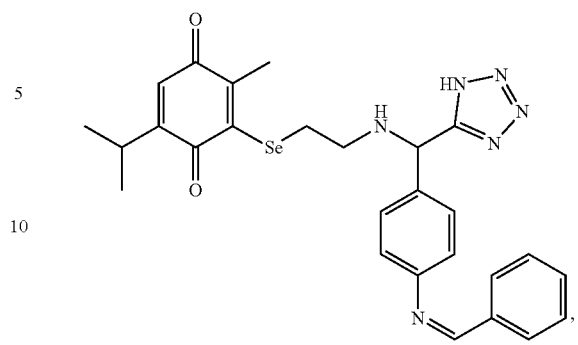
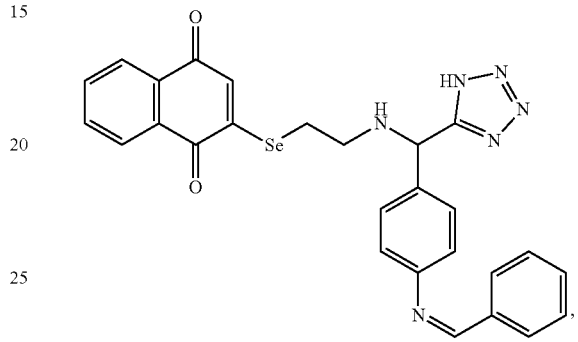
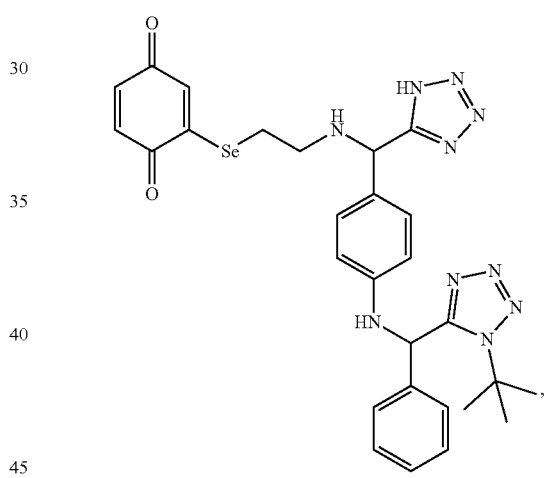
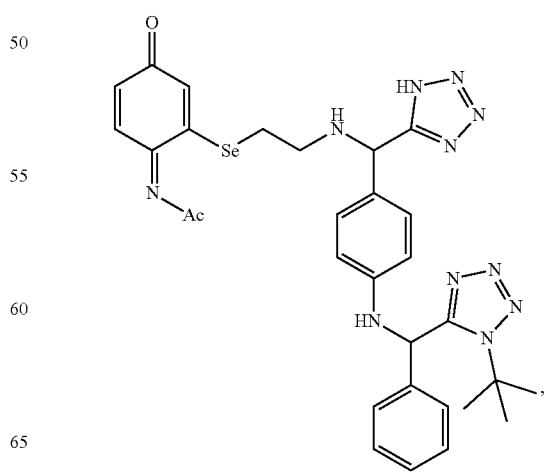

-continued

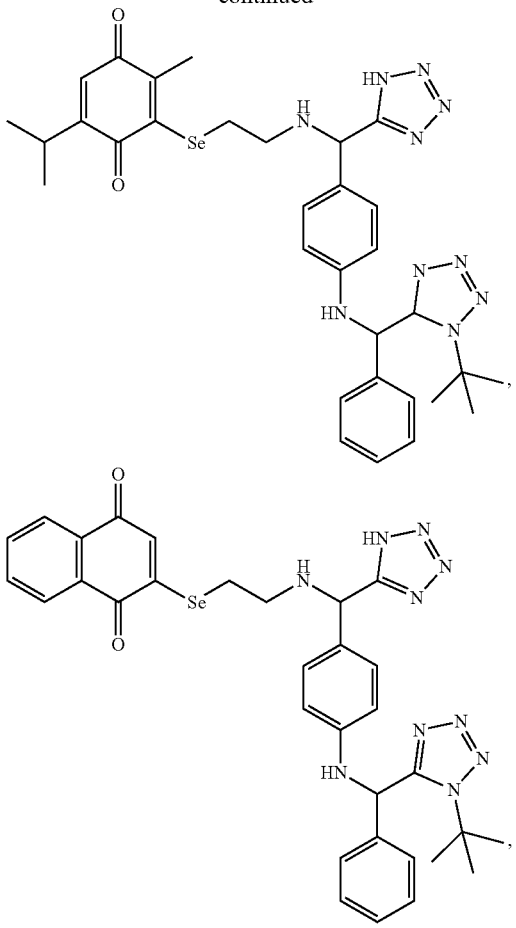

and a pharmaceutically acceptable salt, ester, stereoisomer, or solvate thereof.

12. A compound having the formula I:

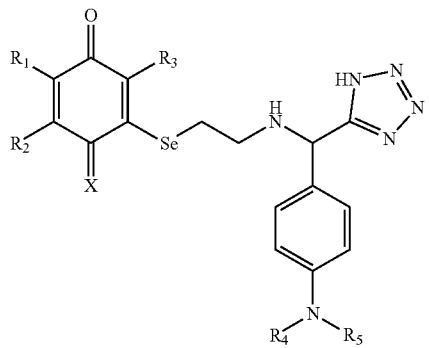

or a pharmaceutically acceptable salt, ester, stereoisomer, or solvate thereof, wherein X is O or $NR_6$, wherein $R_6$ is acetyl;

$R_1$ is hydrogen, $R_2$ is hydrogen or isopropyl, or wherein $R_1$ and $R_2$ can be taken together, along with the carbon atoms to which they are attached, to form a phenyl ring;

$R_3$ is hydrogen or methyl; and $R_4$ is hydrogen, $R_5$ is hydrogen or methyl substituted with a phenyl ring and a tert-butyl substituted tetrazole ring, $R_4$ and $R_5$ are taken together to form a $C_1$ alkenyl substituted with a phenyl ring, or $R_4$ and $R_5$ are taken together, along with the nitrogen atom to which they are attached, to form a maleimide group.

13. A pharmaceutical composition comprising a therapeutically effective amount of the compound of claim 1 and a pharmaceutically acceptable carrier.

14. A pharmaceutical composition comprising a therapeutically effective amount of the compound of claim 1 and a pharmaceutically acceptable carrier.

15. A compound selected from the group consisting of:

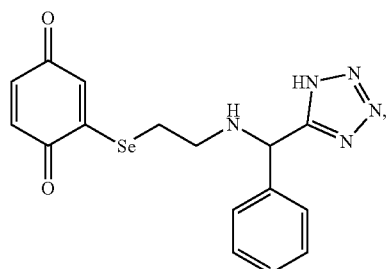

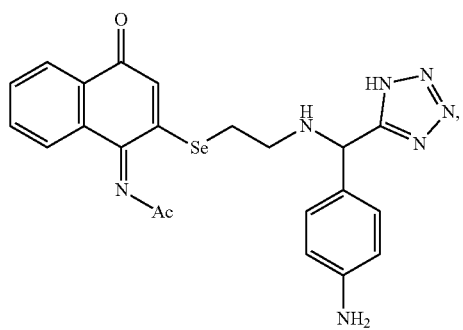

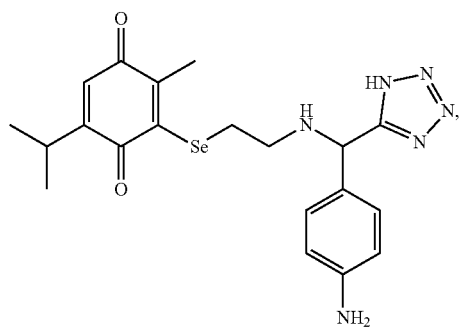

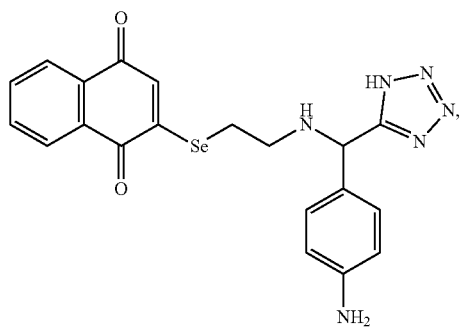

35
-continued
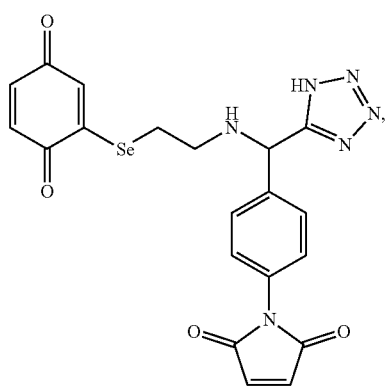
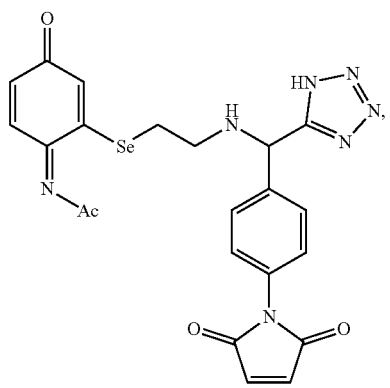
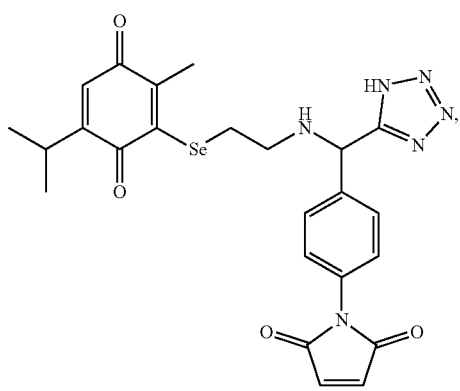
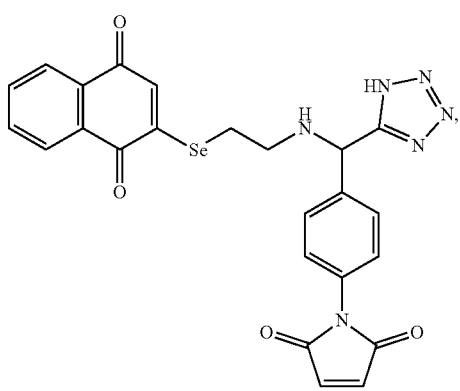
36
-continued
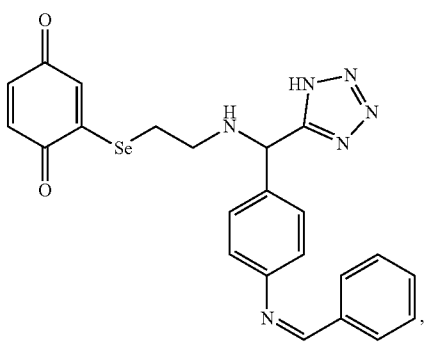
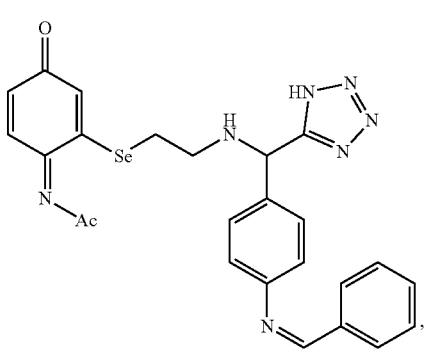
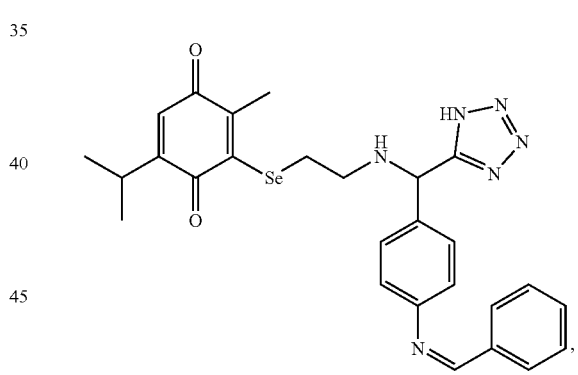
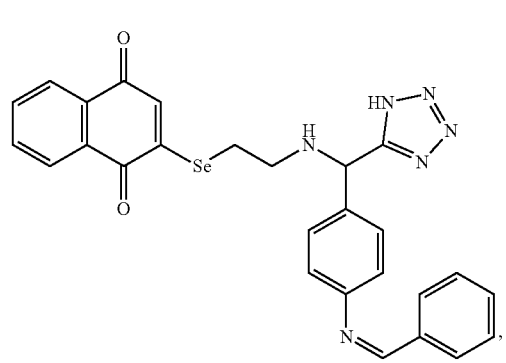

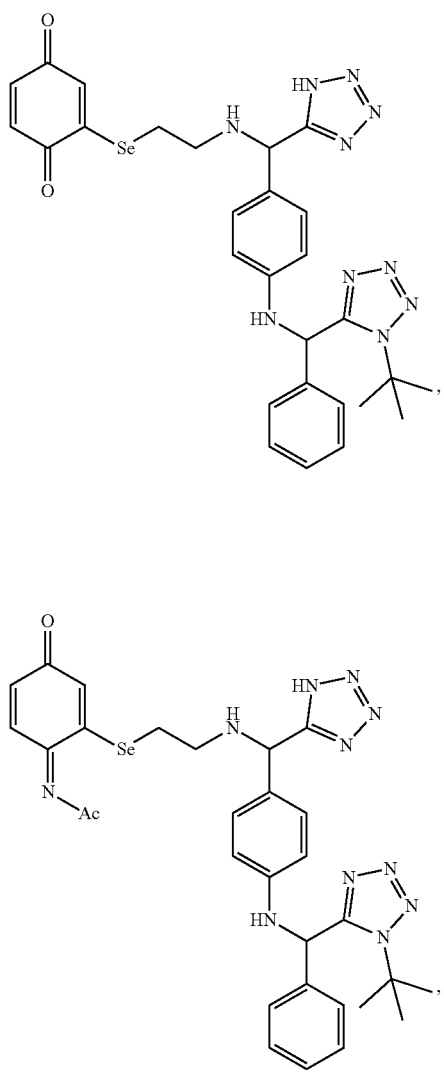
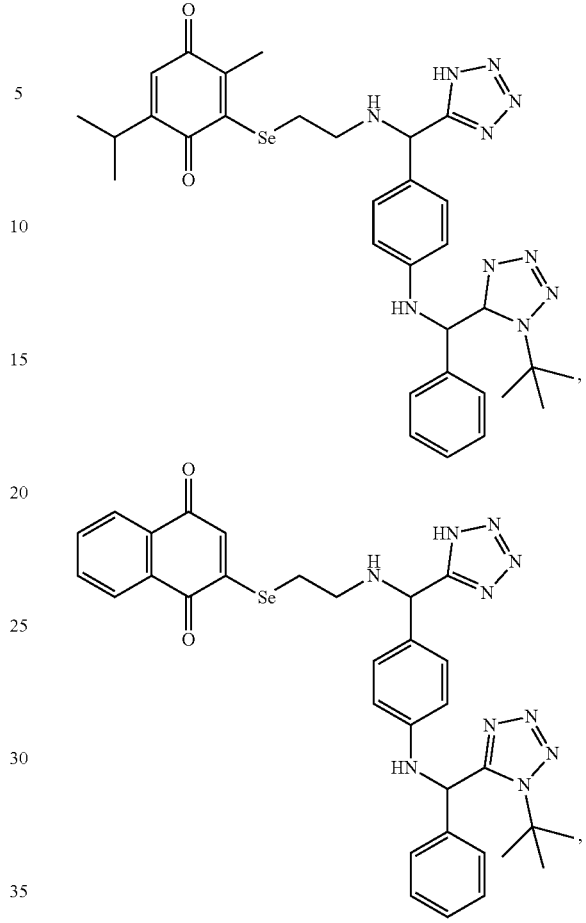
and a pharmaceutically acceptable salt, ester, stereoisomer, or solvate thereof.
16. A pharmaceutical composition comprising a therapeutically effective amount of the compound of claim 15 and a pharmaceutically acceptable carrier.
\* \* \* \* \*